(12) United States Patent
Huang et al.

(10) Patent No.: US 9,579,225 B2
(45) Date of Patent: Feb. 28, 2017

(54) METHODS FOR IMPROVING STENT RETENTION ON A BALLOON CATHETER

(71) Applicant: ABBOTT CARDIOVASCULAR SYSTEMS INC., Santa Clara, CA (US)

(72) Inventors: Bin Huang, Pleasanton, CA (US); David C. Gale, Kennesaw, GA (US); Daniel Castro, Santa Clara, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 0 days.

(21) Appl. No.: 14/552,066

(22) Filed: Nov. 24, 2014

(65) Prior Publication Data

US 2015/0074975 A1 Mar. 19, 2015

Related U.S. Application Data

(63) Continuation of application No. 13/779,636, filed on Feb. 27, 2013, which is a continuation of application
(Continued)

(51) Int. Cl.
*A61F 2/958* (2013.01)
*A61F 2/95* (2013.01)
*B23P 11/00* (2006.01)

(52) U.S. Cl.
CPC ........ *A61F 2/958* (2013.01); *A61F 2002/9505* (2013.01); *A61F 2002/9522* (2013.01); *A61F 2002/9583* (2013.01); *A61F 2002/9586* (2013.01); *B23P 11/005* (2013.01); *Y10T 29/49863* (2015.01); *Y10T 29/49913* (2015.01);
(Continued)

(58) Field of Classification Search
CPC ........ B21D 39/04; B23P 11/005; A61F 2/958; A61F 2002/9522; A61F 2002/9505; A61F 2002/9583; A61F 2002/9586; A61F 2/844; Y10T 29/53987; Y10T 29/49865; Y10T 29/49911; Y10T 29/49913; Y10T 29/49925; Y10T 29/49927; Y10T 29/4994; Y10T 29/49885; Y10T 29/53065; Y10T 29/49776
See application file for complete search history.

(56) References Cited

U.S. PATENT DOCUMENTS 3,687,135 A 8/1972 Stroganov et al.
3,839,743 A 10/1974 Schwarcz
(Continued)

FOREIGN PATENT DOCUMENTS

DE 44 07 079 9/1994
DE 195 09 464 6/1996
(Continued)

OTHER PUBLICATIONS

U.S. Appl. No. 61/016,266, filed Dec. 21, 2007, Mackiewicz.
(Continued)

*Primary Examiner* — Christopher Besler
*Assistant Examiner* — Matthew P Travers
(74) *Attorney, Agent, or Firm* — Baker Botts L.L.P.

(57) ABSTRACT

A method of crimping a stent on a balloon of a catheter assembly is provided. A polymeric stent is disposed over a balloon in an inflated configuration. The stent is crimped over the inflated balloon to a reduced crimped configuration so that the stent is secured onto the balloon. The balloon wall membrane is wedged or pinched between the strut elements of the stent for increasing the retention of the stent on the balloon.

28 Claims, 3 Drawing Sheets

Related U.S. Application Data

No. 13/551,538, filed on Jul. 17, 2012, now Pat. No. 8,925,177, which is a continuation of application No. 11/471,375, filed on Jun. 19, 2006, now Pat. No. 8,333,000.

(52) U.S. Cl.
CPC ..... *Y10T 29/49925* (2015.01); *Y10T 29/49927* (2015.01); *Y10T 29/53065* (2015.01); *Y10T 29/53987* (2015.01)

(56) References Cited

U.S. PATENT DOCUMENTS

| | | |
|---|---|---|
| 3,900,632 A | 8/1975 | Robinson |
| 4,104,410 A | 8/1978 | Malecki |
| 4,110,497 A | 8/1978 | Hoel |
| 4,321,711 A | 3/1982 | Mano |
| 4,346,028 A | 8/1982 | Griffith |
| 4,596,574 A | 6/1986 | Urist |
| 4,599,085 A | 7/1986 | Riess et al. |
| 4,612,009 A | 9/1986 | Drobnik et al. |
| 4,633,873 A | 1/1987 | Dumican et al. |
| 4,656,083 A | 4/1987 | Hoffman et al. |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallsten et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,768,507 A | 9/1988 | Fischell et al. |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,850,999 A | 7/1989 | Planck |
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor |
| 4,902,289 A | 2/1990 | Yannas |
| 4,977,901 A | 12/1990 | Ofstead |
| 4,990,151 A | 2/1991 | Wallsten |
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,062,829 A | 11/1991 | Pryor et al. |
| 5,084,065 A | 1/1992 | Weldon et al. |
| 5,085,629 A | 2/1992 | Goldberg et al. |
| 5,087,244 A | 2/1992 | Wolinsky et al. |
| 5,100,429 A | 3/1992 | Sinofsky et al. |
| 5,104,410 A | 4/1992 | Chowdhary |
| 5,108,417 A | 4/1992 | Sawyer |
| 5,108,755 A | 4/1992 | Daniels et al. |
| 5,112,457 A | 5/1992 | Marchant |
| 5,123,917 A | 6/1992 | Lee |
| 5,147,385 A | 9/1992 | Beck et al. |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,167,614 A | 12/1992 | Tessmann et al. |
| 5,192,311 A | 3/1993 | King et al. |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,292,321 A | 3/1994 | Lee |
| 5,306,286 A | 4/1994 | Stack et al. |
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,423,885 A | 6/1995 | Williams |
| 5,441,515 A | 8/1995 | Khosravi et al. |
| 5,443,458 A | 8/1995 | Eury |
| 5,443,500 A | 8/1995 | Sigwart |
| 5,455,040 A | 10/1995 | Marchant |
| 5,464,650 A | 11/1995 | Berg et al. |
| 5,502,158 A | 3/1996 | Sinclair et al. |
| 5,507,768 A | 4/1996 | Lau et al. |
| 5,514,154 A | 5/1996 | Lau et al. |
| 5,514,379 A | 5/1996 | Weissleder et al. |
| 5,527,337 A | 6/1996 | Stack et al. |
| 5,545,208 A | 8/1996 | Wolff et al. |
| 5,545,408 A | 8/1996 | Trigg et al. |
| 5,549,635 A | 8/1996 | Solar |
| 5,554,120 A | 9/1996 | Chen et al. |
| 5,556,413 A | 9/1996 | Lam |
| 5,569,295 A | 10/1996 | Lam |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,605,696 A | 2/1997 | Eury et al. |
| 5,607,442 A | 3/1997 | Fischell et al. |
| 5,607,467 A | 3/1997 | Froix |
| 5,618,299 A | 4/1997 | Khosravi et al. |
| 5,628,784 A | 5/1997 | Strecker |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,649,977 A | 7/1997 | Campbell |
| 5,667,767 A | 9/1997 | Greff et al. |
| 5,667,796 A | 9/1997 | Otten |
| 5,670,558 A | 9/1997 | Onishi et al. |
| 5,690,644 A | 11/1997 | Yurek et al. |
| 5,693,085 A | 12/1997 | Buirge et al. |
| 5,700,286 A | 12/1997 | Tartaglia et al. |
| 5,707,385 A | 1/1998 | Williams |
| 5,711,763 A | 1/1998 | Nonami et al. |
| 5,716,393 A | 2/1998 | Lindenberg et al. |
| 5,716,981 A | 2/1998 | Hunter et al. |
| 5,725,549 A | 3/1998 | Lam |
| 5,726,297 A | 3/1998 | Gryaznov et al. |
| 5,728,068 A | 3/1998 | Leone et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,881 A | 4/1998 | Patnaik |
| 5,756,457 A | 5/1998 | Wang et al. |
| 5,756,476 A | 5/1998 | Epstein et al. |
| 5,759,474 A | 6/1998 | Rupp et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,776,140 A | 7/1998 | Cottone |
| 5,780,807 A | 7/1998 | Saunders |
| 5,782,839 A | 7/1998 | Hart et al. |
| 5,792,144 A | 8/1998 | Fischell et al. |

(56) References Cited

U.S. PATENT DOCUMENTS

| | | |
|---|---|---|
| 5,800,516 A | 9/1998 | Fine et al. |
| 5,811,447 A | 9/1998 | Kunz et al. |
| 5,824,049 A | 10/1998 | Ragheb et al. |
| 5,830,178 A | 11/1998 | Jones et al. |
| 5,830,461 A | 11/1998 | Billiar et al. |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,836,965 A | 11/1998 | Jendersee et al. |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohthuki et al. |
| 5,855,618 A | 1/1999 | Patnaik et al. |
| 5,858,746 A | 1/1999 | Hubbell et al. |
| 5,860,966 A | 1/1999 | Tower |
| 5,865,814 A | 2/1999 | Tuch |
| 5,868,781 A | 2/1999 | Killion |
| 5,871,468 A | 2/1999 | Kramer et al. |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,743 A | 3/1999 | Ibsen et al. |
| 5,877,263 A | 3/1999 | Patnaik et al. |
| 5,879,713 A | 3/1999 | Roth et al. |
| 5,888,533 A | 3/1999 | Dunn |
| 5,891,192 A | 4/1999 | Murayama et al. |
| 5,893,852 A | 4/1999 | Morales |
| 5,897,955 A | 4/1999 | Drumheller |
| 5,906,759 A | 5/1999 | Richter |
| 5,913,871 A | 6/1999 | Werneth et al. |
| 5,914,182 A | 6/1999 | Drumheller |
| 5,916,870 A | 6/1999 | Lee et al. |
| 5,920,975 A | 7/1999 | Morales |
| 5,922,005 A | 7/1999 | Richter et al. |
| 5,942,209 A | 8/1999 | Leavitt et al. |
| 5,948,428 A | 9/1999 | Lee et al. |
| 5,954,744 A | 9/1999 | Phan et al. |
| 5,957,975 A | 9/1999 | Lafont et al. |
| 5,965,720 A | 10/1999 | Gryaznov et al. |
| 5,971,954 A | 10/1999 | Conway et al. |
| 5,976,181 A | 11/1999 | Whelan et al. |
| 5,976,182 A | 11/1999 | Cox |
| 5,980,530 A | 11/1999 | Willard et al. |
| 5,980,564 A | 11/1999 | Stinson |
| 5,980,928 A | 11/1999 | Terry |
| 5,980,972 A | 11/1999 | Ding |
| 5,981,568 A | 11/1999 | Kunz et al. |
| 5,986,169 A | 11/1999 | Gjunter |
| 5,997,468 A | 12/1999 | Wolff et al. |
| 6,010,445 A | 1/2000 | Armini et al. |
| 6,015,541 A | 1/2000 | Greff et al. |
| 6,022,359 A | 2/2000 | Frantzen |
| 6,042,875 A | 3/2000 | Ding et al. |
| 6,048,964 A | 4/2000 | Lee et al. |
| 6,051,648 A | 4/2000 | Rhee et al. |
| 6,056,993 A | 5/2000 | Leidner et al. |
| 6,060,451 A | 5/2000 | DiMaio et al. |
| 6,063,092 A | 5/2000 | Shin |
| 6,066,156 A | 5/2000 | Yan |
| 6,071,266 A | 6/2000 | Kelley |
| 6,074,381 A | 6/2000 | Dinh et al. |
| 6,074,659 A | 6/2000 | Kunz et al. |
| 6,080,177 A | 6/2000 | Igaki et al. |
| 6,080,488 A | 6/2000 | Hostettler et al. |
| 6,082,990 A | 7/2000 | Jackson et al. |
| 6,083,258 A | 7/2000 | Yadav |
| 6,093,463 A | 7/2000 | Thakrar |
| 6,096,070 A | 8/2000 | Ragheb et al. |
| 6,096,525 A | 8/2000 | Patnaik |
| 6,099,562 A | 8/2000 | Ding et al. |
| 6,103,230 A | 8/2000 | Billiar et al. |
| 6,106,530 A | 8/2000 | Harada |
| 6,107,416 A | 8/2000 | Patnaik et al. |
| 6,110,180 A | 8/2000 | Foreman et al. |
| 6,110,188 A | 8/2000 | Narciso, Jr. |
| 6,113,629 A | 9/2000 | Ken |
| 6,117,979 A | 9/2000 | Hendriks et al. |
| 6,120,522 A | 9/2000 | Vrba et al. |
| 6,120,536 A | 9/2000 | Ding et al. |
| 6,120,904 A | 9/2000 | Hostettler et al. |
| 6,121,027 A | 9/2000 | Clapper et al. |
| 6,125,523 A | 10/2000 | Brown et al. |
| 6,127,173 A | 10/2000 | Eckstein et al. |
| 6,129,761 A | 10/2000 | Hubbell |
| 6,129,928 A | 10/2000 | Sarangapani et al. |
| 6,141,855 A | 11/2000 | Morales |
| 6,150,630 A | 11/2000 | Perry et al. |
| 6,153,252 A | 11/2000 | Hossainy et al. |
| 6,159,227 A | 12/2000 | Di Caprio et al. |
| 6,159,951 A | 12/2000 | Karpeisky et al. |
| 6,160,084 A | 12/2000 | Langer et al. |
| 6,165,212 A | 12/2000 | Dereume et al. |
| 6,166,130 A | 12/2000 | Rhee et al. |
| 6,169,170 B1 | 1/2001 | Gryaznov et al. |
| 6,171,609 B1 | 1/2001 | Kunz |
| 6,174,330 B1 | 1/2001 | Stinson |
| 6,177,523 B1 | 1/2001 | Reich et al. |
| 6,183,505 B1 | 2/2001 | Mohn, Jr. et al. |
| 6,187,013 B1 | 2/2001 | Stoltze et al. |
| 6,187,045 B1 | 2/2001 | Fehring et al. |
| 6,210,715 B1 | 4/2001 | Starling et al. |
| 6,224,626 B1 | 5/2001 | Steinke |
| 6,228,845 B1 | 5/2001 | Donovan et al. |
| 6,240,616 B1 | 6/2001 | Yan |
| 6,245,076 B1 | 6/2001 | Yan |
| 6,245,103 B1 | 6/2001 | Stinson |
| 6,248,344 B1 | 6/2001 | Yianen et al. |
| 6,251,135 B1 | 6/2001 | Stinson et al. |
| 6,251,142 B1 | 6/2001 | Bernacca et al. |
| 6,264,683 B1 | 7/2001 | Stack et al. |
| 6,267,776 B1 | 7/2001 | O'Connell |
| 6,273,913 B1 | 8/2001 | Wright et al. |
| 6,280,412 B1 | 8/2001 | Pederson, Jr. et al. |
| 6,281,262 B1 | 8/2001 | Shikinami |
| 6,284,333 B1 | 9/2001 | Wang et al. |
| 6,287,332 B1 | 9/2001 | Bolz et al. |
| 6,290,721 B1 | 9/2001 | Heath |
| 6,293,966 B1 | 9/2001 | Frantzen |
| 6,296,655 B1 | 10/2001 | Gaudoin et al. |
| 6,303,901 B1 | 10/2001 | Perry et al. |
| 6,312,459 B1 | 11/2001 | Huang et al. |
| 6,327,772 B1 | 12/2001 | Zadno-Azizi et al. |
| 6,352,547 B1 | 3/2002 | Brown et al. |
| 6,375,660 B1 | 4/2002 | Fischell et al. |
| 6,375,826 B1 | 4/2002 | Wang et al. |
| 6,379,381 B1 | 4/2002 | Hossainy et al. |
| 6,387,121 B1 | 5/2002 | Alt |
| 6,388,043 B1 | 5/2002 | Langer et al. |
| 6,395,326 B1 | 5/2002 | Castro et al. |
| 6,409,761 B1 | 6/2002 | Jang |
| 6,423,092 B2 | 7/2002 | Datta et al. |
| 6,461,632 B1 | 10/2002 | Gogolewski |
| 6,464,720 B2 | 10/2002 | Boatman et al. |
| 6,479,565 B1 | 11/2002 | Stanley |
| 6,481,262 B2 | 11/2002 | Ching et al. |
| 6,485,512 B1 | 11/2002 | Cheng |
| 6,492,615 B1 | 12/2002 | Flanagan |
| 6,494,908 B1 | 12/2002 | Huxel et al. |
| 6,495,156 B2 | 12/2002 | Wenz et al. |
| 6,510,722 B1 | 1/2003 | Ching et al. |
| 6,511,748 B1 | 1/2003 | Barrows |
| 6,517,559 B1 | 2/2003 | O'Connell |
| 6,517,888 B1 | 2/2003 | Weber |
| 6,527,801 B1 | 3/2003 | Dutta |
| 6,537,589 B1 | 3/2003 | Chae et al. |
| 6,539,607 B1 | 4/2003 | Fehring et al. |
| 6,540,777 B2 | 4/2003 | Stenzel |
| 6,551,303 B1 | 4/2003 | Van Tassel et al. |

(56) References Cited

U.S. PATENT DOCUMENTS

| | | |
|---|---|---|
| 6,554,854 B1 | 4/2003 | Flanagan |
| 6,565,599 B1 | 5/2003 | Hong et al. |
| 6,569,191 B1 | 5/2003 | Hogan |
| 6,569,193 B1 | 5/2003 | Cox et al. |
| 6,572,672 B2 | 6/2003 | Yadav et al. |
| 6,574,851 B1 | 6/2003 | Mirizzi |
| 6,579,305 B1 | 6/2003 | Lashinski |
| 6,585,755 B2 | 7/2003 | Jackson et al. |
| 6,592,614 B2 | 7/2003 | Lenker et al. |
| 6,592,617 B2 | 7/2003 | Thompson |
| 6,613,072 B2 | 9/2003 | Lau et al. |
| 6,626,939 B1 | 9/2003 | Burnside et al. |
| 6,635,269 B1 | 10/2003 | Jennissen |
| 6,645,243 B2 | 11/2003 | Vallana et al. |
| 6,656,162 B2 | 12/2003 | Santini, Jr. et al. |
| 6,664,335 B2 | 12/2003 | Krishnan |
| 6,666,214 B2 | 12/2003 | Canham |
| 6,667,049 B2 | 12/2003 | Janas et al. |
| 6,669,723 B2 | 12/2003 | Killion et al. |
| 6,676,697 B1 | 1/2004 | Richter |
| 6,679,980 B1 | 1/2004 | Andreacchi |
| 6,689,375 B1 | 2/2004 | Wahlig et al. |
| 6,695,920 B1 | 2/2004 | Pacetti et al. |
| 6,706,273 B1 | 3/2004 | Roessier |
| 6,709,379 B1 | 3/2004 | Brandau et al. |
| 6,719,934 B2 | 4/2004 | Stinson |
| 6,719,989 B1 | 4/2004 | Matsushima et al. |
| 6,720,402 B2 | 4/2004 | Langer et al. |
| 6,745,445 B2 | 6/2004 | Spilka |
| 6,746,773 B2 | 6/2004 | Llanos et al. |
| 6,752,826 B2 | 6/2004 | Holloway et al. |
| 6,753,007 B2 | 6/2004 | Haggard et al. |
| 6,764,504 B2 | 7/2004 | Wang et al. |
| 6,764,505 B1 | 7/2004 | Hossainy et al. |
| 6,769,161 B2 | 8/2004 | Brown et al. |
| 6,818,063 B1 | 11/2004 | Kerrigan |
| 6,846,323 B2 | 1/2005 | Yip et al. |
| 6,863,683 B2 | 3/2005 | Schwager et al. |
| 7,008,446 B1 | 3/2006 | Amis et al. |
| 7,347,869 B2 | 3/2008 | Hojeibane et al. |
| 7,470,281 B2 | 12/2008 | Tedeschi |
| 7,563,400 B2 | 7/2009 | Wilson et al. |
| 7,722,663 B1 | 5/2010 | Austin |
| 7,731,740 B2 | 6/2010 | LaFont et al. |
| 7,763,198 B2 | 7/2010 | Knott et al. |
| 7,776,926 B1 | 8/2010 | Claude et al. |
| 7,947,207 B2 | 5/2011 | Mcniven et al. |
| 8,236,039 B2 | 8/2012 | Mackiewicz |
| 8,309,023 B2 | 11/2012 | Ramzipoor et al. |
| 8,333,000 B2 | 12/2012 | Huang et al. |
| 2001/0001128 A1 | 5/2001 | Holman et al. |
| 2001/0044652 A1 | 11/2001 | Moore |
| 2002/0002399 A1 | 1/2002 | Huxel et al. |
| 2002/0004060 A1 | 1/2002 | Heublein et al. |
| 2002/0004101 A1 | 1/2002 | Ding et al. |
| 2002/0007207 A1 | 1/2002 | Shin et al. |
| 2002/0035774 A1 | 3/2002 | Austin |
| 2002/0062148 A1 | 5/2002 | Hart |
| 2002/0065553 A1 | 5/2002 | Weber |
| 2002/0068967 A1 | 6/2002 | Drasler et al. |
| 2002/0111590 A1 | 8/2002 | Davila et al. |
| 2002/0116050 A1 | 8/2002 | Kocur |
| 2002/0138127 A1 | 9/2002 | Stiger et al. |
| 2002/0138133 A1 | 9/2002 | Lenz et al. |
| 2002/0161114 A1 | 10/2002 | Gunatillake et al. |
| 2003/0033001 A1 | 2/2003 | Igaki |
| 2003/0040772 A1 | 2/2003 | Hyodoh et al. |
| 2003/0055482 A1 | 3/2003 | Schwager et al. |
| 2003/0056360 A1 | 3/2003 | Brown et al. |
| 2003/0093107 A1 | 5/2003 | Parsonage et al. |
| 2003/0097172 A1 | 5/2003 | Shalev et al. |
| 2003/0100865 A1 | 5/2003 | Santini, Jr. et al. |
| 2003/0105518 A1 | 6/2003 | Dutta |
| 2003/0105530 A1 | 6/2003 | Pirhonen et al. |
| 2003/0171053 A1 | 9/2003 | Sanders |
| 2003/0187495 A1 | 10/2003 | Cully et al. |
| 2003/0208227 A1 | 11/2003 | Thomas |
| 2003/0208259 A1 | 11/2003 | Penhasi |
| 2003/0209835 A1 | 11/2003 | Chun et al. |
| 2003/0212450 A1 | 11/2003 | Schlick |
| 2003/0226833 A1 | 12/2003 | Shapovalov et al. |
| 2003/0236563 A1 | 12/2003 | Fifer |
| 2004/0073155 A1 | 4/2004 | Laufer et al. |
| 2004/0093077 A1 | 5/2004 | White et al. |
| 2004/0098095 A1 | 5/2004 | Burnside et al. |
| 2004/0106973 A1* | 6/2004 | Johnson ............... A61F 2/958 623/1.11 |
| 2004/0111149 A1 | 6/2004 | Stinson |
| 2004/0127880 A1 | 7/2004 | Weber |
| 2004/0133263 A1 | 7/2004 | Dusbabek et al. |
| 2004/0138731 A1 | 7/2004 | Johnson |
| 2004/0143317 A1 | 7/2004 | Stinson et al. |
| 2004/0167610 A1 | 8/2004 | Fleming, III |
| 2004/0199246 A1 | 10/2004 | Chu et al. |
| 2005/0096735 A1 | 5/2005 | Hojeibane et al. |
| 2005/0118344 A1 | 6/2005 | Pacetti |
| 2005/0143752 A1 | 6/2005 | Schwager et al. |
| 2005/0154450 A1 | 7/2005 | Larson et al. |
| 2005/0183259 A1 | 8/2005 | Eidenschink et al. |
| 2005/0203606 A1 | 9/2005 | VanCamp |
| 2005/0267408 A1 | 12/2005 | Grandt et al. |
| 2005/0283962 A1 | 12/2005 | Boudjemline |
| 2006/0004328 A1 | 1/2006 | Joergensen et al. |
| 2006/0020285 A1 | 1/2006 | Niermann |
| 2006/0030923 A1 | 2/2006 | Gunderson |
| 2006/0041271 A1 | 2/2006 | Bosma et al. |
| 2006/0047336 A1 | 3/2006 | Gale et al. |
| 2006/0058863 A1 | 3/2006 | LaFont et al. |
| 2006/0100694 A1 | 5/2006 | Globerman |
| 2006/0229712 A1 | 10/2006 | Wilson et al. |
| 2006/0287708 A1 | 12/2006 | Ricci et al. |
| 2006/0288561 A1 | 12/2006 | Roach et al. |
| 2007/0006441 A1 | 1/2007 | Mcniven et al. |
| 2007/0204455 A1 | 9/2007 | Knott et al. |
| 2007/0208370 A1 | 9/2007 | Hauser et al. |
| 2007/0255388 A1 | 11/2007 | Rudakov et al. |
| 2007/0289117 A1 | 12/2007 | Huang et al. |
| 2008/0097570 A1 | 4/2008 | Thornton et al. |
| 2008/0208118 A1 | 8/2008 | Goldman |
| 2009/0076448 A1 | 3/2009 | Consigny et al. |
| 2009/0105747 A1 | 4/2009 | Chanduszko et al. |
| 2009/0187210 A1 | 7/2009 | Mackiewicz |
| 2009/0187211 A1 | 7/2009 | Mackiewicz |
| 2009/0292347 A1 | 11/2009 | Asmus et al. |
| 2010/0152765 A1 | 6/2010 | Haley |
| 2011/0106234 A1 | 5/2011 | Grandt |
| 2011/0257675 A1 | 10/2011 | Mackiewicz |
| 2012/0035704 A1 | 2/2012 | Grandt |
| 2012/0259402 A1 | 10/2012 | Grandt |
| 2012/0283814 A1 | 11/2012 | Huang et al. |
| 2013/0239396 A1 | 9/2013 | Schwager et al. |
| 2013/0269168 A1 | 10/2013 | Huang et al. |

FOREIGN PATENT DOCUMENTS

| | | |
|---|---|---|
| DE | 197 31 021 | 1/1999 |
| DE | 198 56 983 | 12/1999 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0 716 836 | 6/1996 |
| EP | 0 787 020 | 8/1997 |
| EP | 0 935 952 | 8/1999 |
| EP | 0 970 711 | 1/2000 |

(56) References Cited

FOREIGN PATENT DOCUMENTS

| | | |
|---|---|---|
| EP | 1 000 591 | 5/2000 |
| EP | 1 226 798 | 7/2002 |
| EP | 1 295 570 | 3/2003 |
| EP | 1 637 177 | 3/2006 |
| EP | 2 029 052 | 3/2009 |
| EP | 2 196 174 | 6/2010 |
| EP | 2 322 118 | 5/2011 |
| GB | 2 247 696 | 3/1992 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/29647 | 11/1995 |
| WO | WO 98/04415 | 2/1998 |
| WO | WO 99/03515 | 1/1999 |
| WO | WO 99/16382 | 4/1999 |
| WO | WO 99/16386 | 4/1999 |
| WO | WO 99/42147 | 8/1999 |
| WO | WO 99/55255 | 11/1999 |
| WO | WO 00/12147 | 3/2000 |
| WO | WO 00/64506 | 11/2000 |
| WO | WO 00/78249 | 12/2000 |
| WO | WO 01/01890 | 1/2001 |
| WO | WO 01/05462 | 1/2001 |
| WO | WO 01/21110 | 3/2001 |
| WO | WO 02/102283 | 12/2002 |
| WO | WO 2004/023985 | 3/2004 |
| WO | WO 2004/047681 | 6/2004 |
| WO | WO 2005/053937 | 6/2005 |
| WO | WO 2006/110861 | 10/2006 |
| WO | WO 2007/061927 | 5/2007 |
| WO | WO 2008/024491 | 2/2008 |
| WO | WO 2008/024621 | 2/2008 |
| WO | WO 2008/033621 | 3/2008 |
| WO | WO 2009/066330 | 5/2009 |
| WO | WO 2009/086205 | 7/2009 |
| WO | WO 2010/066446 | 6/2010 |
| WO | WO 2011/050979 | 5/2011 |

OTHER PUBLICATIONS

U.S. Appl. No. 61/138,455, filed Dec. 17, 2008, Haley.
U.S. Appl. No. 13/502,084, filed Oct. 29, 2010, Grandt.
U.S. Appl. No. 13/779,636, filed Feb. 27, 2013.
U.S. Appl. No. 09/957,216, Jan. 21, 2005 Issue Fee Payment.
U.S. Appl. No. 09/957,216, Feb. 16, 2005 Issue Notification.
U.S. Appl. No. 09/957,216, Nov. 4, 2004 Notice of Allowance.
U.S. Appl. No. 09/957,216, Sep. 17, 2004 Response to Non-Final Office Action.
U.S. Appl. No. 09/957,216, Jun. 14, 2004 Non-Final Office Action.
U.S. Appl. No. 09/957,216, Mar. 8, 2004 Response to Non-Final Office Action.
U.S. Appl. No. 09/957,216, Sep. 26, 2003 Non-Final Office Action.
U.S. Appl. No. 09/957,216, Aug. 4, 2003 Response to Restriction Requirement.
U.S. Appl. No. 09/957,216, Jun. 10, 2003 Restriction Requirement.
U.S. Appl. No. 11/064,692, Apr. 1, 2015 Non-Final Office Action.
U.S. Appl. No. 11/064,692, Nov. 24, 2014 Amendment and Request for Continued Examination (RCE).
U.S. Appl. No. 11/064,692, Aug. 26, 2014 Final Office Action.
U.S. Appl. No. 11/064,692, Jan. 7, 2014 Amendment and Request for Continued Examination (RCE).
U.S. Appl. No. 11/064,692, Feb. 25, 2014 Non-Final Office Action.
U.S. Appl. No. 11/064,692, Oct. 2, 2013 Final Office Action.
U.S. Appl. No. 11/064,692, Sep. 10, 2013 Response to Non-Final Office Action.
U.S. Appl. No. 11/064,692, May 10, 2013 Non-Final Office Action.
U.S. Appl. No. 11/064,692, Nov. 2, 2011 Amendment and Request for Continued Examination (RCE).
U.S. Appl. No. 11/064,692, Aug. 2, 2011 Final Office Action.
U.S. Appl. No. 11/064,692, Jun. 29, 2011 Response to Non-Final Office Action.
U.S. Appl. No. 11/064,692, Mar. 29, 2011 Non-Final Office Action.
U.S. Appl. No. 11/064,692, Feb. 23, 2010 Amendment and Request for Continued Examination (RCE).
U.S. Appl. No. 11/064,692, Nov. 23, 2009 Final Office Action.
U.S. Appl. No. 11/064,692, Jul. 31, 2009 Response to Non-Final Office Action.
U.S. Appl. No. 11/064,692, Mar. 31, 2009 Non-Final Office Action.
U.S. Appl. No. 11/064,692, Feb. 17, 2009 Amendment and Request for Continued Examination (RCE).
U.S. Appl. No. 11/064,692, Oct. 14, 2008 Final Office Action.
U.S. Appl. No. 11/064,692, Jul. 21, 2008 Response to Non-Final Office Action.
U.S. Appl. No. 11/064,692, Feb. 21, 2008 Non-Final Office Action.
U.S. Appl. No. 11/471,375, Nov. 14, 2012 Issue Fee payment.
U.S. Appl. No. 11/471,375, Aug. 17, 2012 Notice of Allowance.
U.S. Appl. No. 11/471,375, Jun. 12, 2012 Response to Final Office Action.
U.S. Appl. No. 11/471,375, Apr. 13, 2012 Final Office Action.
U.S. Appl. No. 11/471,375, Mar. 8, 2012 Response to Non-Final Office Action.
U.S. Appl. No. 11/471,375, Dec. 8, 2011 Non-Final Office Action.
U.S. Appl. No. 11/471,375, Jun. 16, 2011 Response to Non-Final Office Action.
U.S. Appl. No. 11/471,375, Mar. 16, 2011 Non-Final Office Action.
U.S. Appl. No. 11/471,375, Jan. 18, 2011 Amendment and Request for Continued Examination (RCE).
U.S. Appl. No. 11/471,375, Sep. 15, 2010 Final Office Action.
U.S. Appl. No. 11/471,375, Aug. 20, 2010 Response to Non-Final Office Action.
U.S. Appl. No. 11/471,375, Aug. 5, 2010 Non-Final Office Action.
U.S. Appl. No. 11/471,375, Mar. 29, 2010 Response to Non-Final Office Action.
U.S. Appl. No. 11/471,375, Feb. 2, 2010 Non-Final Office Action.
U.S. Appl. No. 11/471,375, Oct. 6, 2009 Response to Non-Final Office Action.
U.S. Appl. No. 11/471,375, Jul. 6, 2009 Non-Final Office Action.
U.S. Appl. No. 13/551,538, Nov. 13, 2013 Final Office Action.
U.S. Appl. No. 13/551,538, Sep. 10, 2013 Response to Non-Final Office Action.
U.S. Appl. No. 13/551,538, Jun. 10, 2013 Non-Final Office Action.
U.S. Appl. No. 13/551,538, Apr. 15, 2014 Non-Final Office Action.
U.S. Appl. No. 13/779,636, Dec. 18, 2013 Non-Final Office Action.
U.S. Appl. No. 13/779,636, Aug. 22, 2014 Final Office Action.
U.S. Appl. No. 13/779,636, Nov. 24, 2014 Amendment and Request for Continued Examination (RCE).
U.S. Appl. No. 13/779,636, Dec. 29, 2014 Non-Final Office Action.
Anonymous, "Bioabsorbable stent mounted on a catheter having optical coherence tomography capabilities", *Research Disclosure*, pp. 1159-1162, (2004).
Ansari, "End-to-end tubal anastomosis using an absorbable stent", *Fertility and Sterility*, 32(2):197-201 (1979).
Ansari, "Tubal Reanastomosis Using Absorbable Stent", *International Journal of Fertility*, 23(4):242-243 (1978).
Bull, "Parylene Coating for Medical Applications", *Medical Product Manufacturing News*, 18:1 (1993).
Casper, et al., "Fiber-Reinforced Absorbable Composite for Orthopedic Surgery", *Polymeric Materials Science and Engineering*, 53:497-501 (1985).
Detweiler, et al., "Gastrointestinal Sutureless Anastomosis Using Fibrin Glue: Reinforcement of the Sliding Absorbable Intraluminal Nontoxic Stent and Development of a Stent Placement Device", *Journal of Investigative Surgery*, 9(2):111-130 (1996).
Detweiler, et al., "Sliding, Absorbable, Reinforced Ring and an Axially Driven Stent Placement Device for Sutureless Fibrin Glue Gastrointestinal Anastomisis ", *Journal of Investigative Surgery*, 9(6):495-504 (1996).

(56) References Cited

OTHER PUBLICATIONS

Detweiler, et al., "Sutureless Anastomosis of the Small Intestine and the Colon in Pigs Using an Absorbable Intraluminal Stent and Fibrin Glue", *Journal of Investigative Surgery*, 8(2):129-140 (1995).
Detweiler, et al., "Sutureless Cholecystojejunostomu in Pigs Using an Absorbable Intraluminal Stent and Fibrin Glue", *Journal of Investigative Surgery*, 9(1):13-26 (1996).
Devanathan, et al., "Polymeric Conformal Coatings for Implantable Electronic Devices", *IEEE Transactions on Biomedical Engineering*, BME-27(11):671-675 (1980).
Elbert, et al., "Conjugate Addition Reactions Combined with Free-Radical Cross-Linking for the Design of Materials for Tissue Engineering", *Biomacromolecules*, 2(2):430-441 (2001).
Hahn, et al., "Biocompatibility of Glow-Discharge-Polymerized Films and Vacuum-Deposited Parylene", *J Applied Polymer Sci*, 38:55-64 (1984).
Hahn, et al., "Glow Discharge Polymers as Coatings for Implanted Devices", *ISA*, pp. 109-111 (1981).
He, et al., "Assessment of Tissue Blood Flow Following Small Artery Welding with a Intraluminal Dissolvable Stent", *Microsurgery*, 19(3):148-152 (1999).
Kelley, et al., "Totally Resorbable High-Strength Composite Material", *Advances in Biomedical Polymers*, 35:75-85 (1987).
Kubies, et al., "Microdomain Structure in polylactide-*block*-poly-(ethylene oxide) copolymer films", *Biomaterials*, 21(5):529-536 (2000).
Kutryk, et al., "Coronary Stenting: Current Perspectives", *a companion to the Handbook of Coronary Stents*, pp. 1-16 (1999).
Martin, et al., "Enhancing the biological activity of immobilized osteopontin using a type-1 collagen affinity coating", *J. Biomed. Mater Res*, 70A:10-19 (2004).
Mauduit, et al., "Hydrolytic degradation of films prepared from blends of high and low molecular weight poly(DL-lactic acid)s", *J. Biomed. Mater. Res.*, 30(2):201-207 (1996).
Middleton, et al., "Synthetic biodegradable polymers as orthopedic devices", *Biomaterials*, 21(23):2335-2346 (2000).
Muller, et al., "Advances in Coronary Angioplasty: Endovascular Stents", *Coron. Anter. Dis.*, 1(4):438-448 (1990).
Nichols, et al., "Electrical Insulation of Implantable Devices by Composite Polymer Coatings", *ISA Transactions*, 26(4):15-18 (1987).
Peuster, et al., "A novel approach to temporary stenting: degradable cardiovascular stents produced from corrodible metal-results 6-18 months after implantation into New Zealand white rabbits", *Heart*, 86(5):563-569 (2001).
Pietrzak, et al., "Bioabsorbable Fixation Devices: Status for the Craniomaxillofacial Surgeon", *J. Craniofaxial Surg.*, 8(2):92-96 (1997).
Pietrzak, et al., "Bioresorbable implants—practical considerations", *Bone*, 19(1):109S-119S (Supplement Jul. 1996).
Redman, "Clinical Experience with Vasovasostomy Utilizing Absorbable Intravasal Stent", *Urology*, 20(1):59-61 (1982).
Rust, et al., "The Effect of Absorbable Stenting on Postoperative Stenosis of the Surgically Enlarged Maxillary Sinus Ostia in a Rabbit Animal Model", *Archives of Otolaryngology*, 122(12):1395-1397 (1996).
Schatz, "A View of Vascular Stants", *Circulation*, 79(2):445-457 (1989).
Schmidt, et al., "Long-Term Implants of Parylene-C Coated Microelectrodes", *Med & Biol Eng & Comp*, 26(1):96-101 (1988).
Spagnuolo, et al., "Gas 1 is induced by VE-cadherin and vascular endothelial growth factor and inhibits endothelial cell apoptosis", *Blood*, 103(8):3005-3012 (2004).
Tamai, et al., "Initial and 6-Month Results of Biodegradable Poly-I-Lactic Acid Coronary Stents in Humans", *Circulation*, 102(4):399-404 (2000).
Tsuji, et al., "Biodegradable Polymeric Stents", *Current Interventional Cardiology Reports*, 3(1):10-17 (2001).
Völkel, et al., "Targeting of immunoliposomes to endothelial cells using a single-chain Fv fragment directed against human endoglin(CD105)", *Biochimica et Biophysica Acta*, 1663(1-2):158-166 (2004).
Von Recum, et al., "Degradation of polydispersed poly(L-lactic acid) to modulate lactic acid release", *Biomaterials*, 16(6):441-445 (1995).
Yau, et al., "Modern Size-Exclusion Liquid Chromatography", *Wiley-Interscience Publication*, Table of Contents IX-XV (1979).
European Search Report for EP Application No. 07809699.7, dated Jun. 12, 2009.
International Search Report for PCT/US2007/014331, dated Dec. 28, 2007.
U.S. Appl. No. 13/551,538, filed Jul. 17, 2012, Huang et al.
U.S. Appl. No. 13/779,683, Jun. 27, 2014 Applicant Initiated Interview Summary.
U.S. Appl. No. 13/779,636, Mar. 30, 2015 Response to Non-Final Office Action.
U.S. Appl. No. 13/779,636, Jun. 5, 2015 Final Office Action.
U.S. Appl. No. 13/551,538, Jun. 19, 2014 Applicant Initiated Interview Summary.
U.S. Appl. No. 13/551,538, Jul. 15, 2014 Response to Non-Final Office Action.
U.S. Appl. No. 13/551,538, Sep. 19, 2014 Notice of Allowance.
U.S. Appl. No. 13/551,538, Nov. 24, 2014 Issue Fee Payment.
U.S. Appl. No. 11/064,692, Jul. 25, 2014 Response to Non-Final Office Action.
U.S. Appl. No. 11/064,692, Jan. 15, 2014 Response to Non-Final Office Action.
European Opposition dated Feb. 7, 2015 against European Patent EP 2066263.

* cited by examiner

METHODS FOR IMPROVING STENT RETENTION ON A BALLOON CATHETER

REFERENCE TO RELATED APPLICATIONS

This application is a continuation of U.S. patent application Ser. No. 13/779,636, filed on Feb. 27, 2013, which is a continuation of U.S. patent application Ser. No. 13/551,538, filed on Jul. 17, 2012, which is a continuation application of U.S. patent application Ser. No. 11/471,375, filed on Jun. 19, 2006, and which issued as U.S. Pat. No. 8,333,000 on Dec. 18, 2012.

TECHNICAL FIELD

This invention relates to methods of crimping or mounting a stent on a balloon of a catheter assembly.

BACKGROUND

A stent, as illustrated in FIG. 1, is an intravascular prosthesis that is delivered and implanted within a patient's vasculature or other bodily cavities and lumens by a balloon catheter. For example, stents can be used in percutaneous transluminal coronary angioplasty (PTCA) or percutaneous transluminal angioplasty (PTA). Conventional stents and catheters are disclosed by U.S. Pat. Nos. 4,733,665, 4,800,882, 4,886,062, 5,514,154, 5,569,295, and 5,507,768. In advancing a stent through a body vessel to a deployment site, the stent must be able to securely maintain its axial as well as rotational position on the delivery catheter without translocating proximally or distally, and especially without becoming separated from the catheter. Stents that are not properly secured or retained to the catheter may slip and either be lost or be deployed in the wrong location. The stent must be "crimped" in such a way as to minimize or prevent distortion of the stent and to thereby prevent abrasion and/or reduce trauma to the vessel walls.

Generally, stent crimping is the act of affixing the stent to the delivery catheter or delivery balloon so that it remains affixed to the catheter or balloon until the physician desires to deliver the stent at the treatment site. Current stent crimping technology is sophisticated. Examples of such technology which are known by one of ordinary skill the art include a roll crimper; a collet crimper; and an iris or sliding-wedge crimper. To use a roll crimper, first the stent is slid loosely onto the balloon portion of the catheter. This assembly is placed between the plates of the roll crimper. With an automated roll crimper, the plates come together and apply a specified amount of force. They then move back and forth a set distance in a direction that is perpendicular to the catheter. The catheter rolls back and forth this motion, and the diameter of the stent is reduced. The process can be broken down into more than one step, each with its own level of force, translational distance, and number of cycles. This process imparts a great deal of shear to the stent in a direction perpendicular to the catheter or catheter wall. Furthermore, as the stent is crimped, there is additional relative motion between the stent surface and the crimping plates.

The collet crimper is equally conceptually simple. A standard drill-chuck collet is equipped with several pie-piece-shaped jaws. These jaws move in a radial direction as an outer ring is turned. To use this crimper, a stent is loosely placed onto the balloon portion of a catheter and inserted in the center space between the jaws. Turning the outer ring causes the jaws to move inward. An issue with this device is determining or designing the crimping endpoint. One scheme is to engineer the jaws so that when they completely close, they touch and a center hole of a known diameter remains. Using this approach, turning the collet onto the collet stops crimps the stent to the known outer diameter. While this seems ideal, it can lead to problems. Stent struts have a tolerance on their thickness. Additionally, the process of folding non-compliant balloons is not exactly reproducible. Consequently, the collet crimper exerts a different amount of force on each stent in order to achieve the same final dimension. Unless this force, and the final crimped diameter, is carefully chosen, the variability of the stent and balloon dimensions can yield stent or balloon damage.

In the sliding wedge or iris crimper, adjacent sections move inward and twist, much like the leaves in a camera aperture. This crimper can be engineered to have two different types of endpoints. It can stop at a final diameter, or it can apply a fixed force and allow the final diameter to float from the discussion on the collet crimper, there are advantages in applying a fixed level of force as variability in strut and balloon dimension will not change the crimping force. The sliding wedges impart primarily normal forces. As the wedges slide over each other, they impart some tangential force. Lastly, the sliding wedge crimper presents a nearly cylindrical inner surface to the stent, even as it crimps. This means the crimping loads are distributed over the entire outer surface of the stent.

All current stent crimping methods were developed for all-metal stents. Stent metals, such as stainless steel, are durable and can take abuse. When crimping is too severe, it usually damages the underlying balloon, not the metal stent. But polymeric stents present different challenges. A polymer stent requires relatively wider struts than metal stents so as to provide suitable mechanical properties, such as radial strength. At the crimping stage, less space is provided between the struts which can result in worse stent retention than a metallic stent. Moreover, the use of high processing temperature during the crimping process to enhance stent retention may not be possible as a polymeric stent may have a glass transition temperature generally equivalent to the glass transition temperature of the balloon. Higher processing temperatures may cause the stent to lose some of its preferred mechanical properties.

The present invention provides a novel method of crimping a stent, more specifically a polymeric stent on an expandable member or a balloon.

SUMMARY

In accordance with one embodiment, a method of crimping a stent on a balloon of a catheter assembly is provided, comprising: providing a polymeric stent disposed over a balloon in an inflated configuration; and crimping the stent over the inflated balloon to a reduced crimped configuration so that the stent is secured onto the balloon. In some embodiments, the act of providing comprises inserting a balloon in a collapsed configuration into a stent; and expanding the balloon to the inflated configuration, wherein the inflated configuration is equal to or less than the intended expansion configuration of the balloon. In some embodiments, the inflated configuration is a configuration which provides for a membrane or wall of the balloon to protrude into gaps between structural elements of the stent. As a result, subsequent to crimping the stent on the balloon, a membrane or wall of the balloon is pinched or wedged between the structural elements of the stent. During the crimping process, the pressure in the balloon can be controllably released by a valve. In some embodiments, the stent is not a metallic stent. In some embodiments, the stent is a biodegradable polymeric stent. In some embodiments, the stent is a biodegradable polymeric stent with or without a biodegradable metallic component.

In accordance with another embodiment, a method of crimping a stent on a balloon, is provided comprising the following acts in the order as listed: (a) providing a stent disposed over a balloon in an inflated configuration; (b) crimping the stent to a first reduced diameter; (c) at least partially deflating the balloon; (d) inflating the balloon to at least an inner diameter of the stent; and (e) crimping the stent to a second reduced diameter. The second reduced diameter can be the final crimped diameter.

DESCRIPTION OF FIGURES

The figures have not been drawn to scale and portions thereof have been under or over emphasized for illustrative purposes.

FIGS. 2A, 2B1, 2B2, 2C, 2D, and 2E (collectively referred to as FIG. 2) illustrate methods for crimping a stent on a balloon of a catheter;

DESCRIPTION

The stent crimping methods are suitable to adequately and uniformly crimp a balloon expandable stent onto a balloon or expandable member of a catheter assembly. The embodiments of the invention are also applicable to self-expandable stents and stent-grafts. In one embodiment, the method of the present invention is particularly directed to crimping of a biodegradable, polymeric stent on a balloon of a catheter assembly. A biodegradable polymer stent has many advantages over metal stents, including the ability to be placed in the body only for the duration of time until the intended function of the stent has been performed. However, retention of a polymer stent has been proven to be more challenging than that of a metallic stent. Polymer stents can require wider struts than metal stents so as to provide suitable mechanical properties, such as radial strength, for the stent. At the crimping stage, less space is provided between the struts which can result in worse stent retention than a metallic stent. Moreover, the use of high processing temperature during the crimping process to enhance stent retention may not be possible as a polymeric stent may have a glass transition temperature generally equivalent to, or lower than the glass transition temperature of the balloon. Higher processing temperatures may cause the polymeric stent to lose some of its preferred mechanical properties.

Figure 2A:
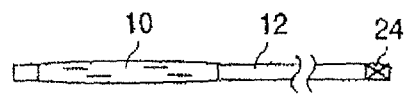

FIG. 2A illustrates an expandable member, such as a balloon 10, integrated at a distal end of a catheter assembly 12. In some embodiments, the balloon 10 is intended to include any type of enclosed member such as an elastic type member that is selectively inflatable to dilate from a collapsed configuration to a desired and controlled expanded configuration. The balloon 10 should also be capable of being deflated to a reduced profile or back to its original collapsed configuration. The balloon 10 can be made from any suitable type of material and can be of any thickness so long as the ability to crimp the stent on to the balloon and optimum performance capabilities of the balloon are not adversely compromised. Performance properties include, for example, high burst strength, good flexibility, high resistance to fatigue, an ability to fold, and ability to cross and re-cross a desired region of treatment or an occluded region in a bodily lumen, and a low susceptibility to defects caused by handling and crimping, among other possibilities.

The balloon is illustrated in FIG. 2A in a collapsed configuration. The collapsed configuration can be the configuration that is conventionally used during the process of crimping of a stent on a balloon. The balloon 10 includes no liquid or gas in the internal chamber of the balloon 10 and includes regions where the balloon material is folded over giving the balloon a crease-like appearance. Such collapsed configuration can be the configuration of introduction and navigation of the balloon 10 in the vascular system of a patient.

Figure 1:
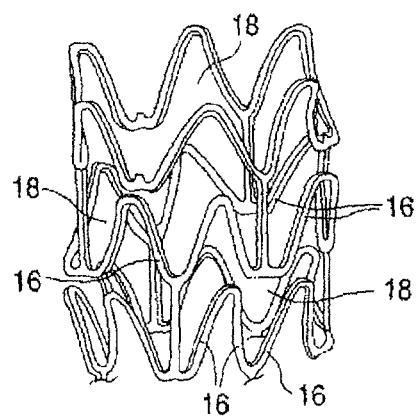
FIG. 1 illustrates an example of a stent.

As illustrated in FIG. 2B 1, a stent 14 is positioned over the balloon 10. The stent 14 is illustrated to have struts 16 separated by gaps 18 (as can also be seen in FIG. 1). In some embodiments, the diameter of the stent 14 as positioned over the collapsed balloon 10 is much larger than the collapsed diameter of the balloon 10. In some embodiments, as illustrated in FIG. 2B2, the diameter of the stent 14 is large enough so that an operator is capable of slipping the stent 14 over the balloon 10 with minimal gap or space between the balloon 10 and the stent 14. The balloon 10 can be inflated to a crimp inflation state before being placed into a crimping device 20 (FIG. 2D) or after being placed into the crimping device 20. The crimp inflation state is a state greater than the collapsed configuration and is a state equal to or less than the intended expansion configuration or use state. The intended expansion configuration is defined as inflation of a balloon to a diameter or size within the range of its intended use or design. The intended expanded configuration is provided by the manufacturer of the balloon or can be determined by one having ordinary skill in the art and is intended to include the range of diameter of use or the range of pressure to be applied for the planned performance of the balloon. In some embodiments, the balloon's intended use state is up to the threshold inflated configuration where the balloon becomes damaged or disapproved for use if the balloon was inflated more.

The balloon 10 can be inflated by application of a fluid or a gas. The temperature of the fluid or gas can be adjusted to other than ambient or room temperature. In one embodiment, a heated fluid or gas is used. In some embodiments, heated can be defined as above 25 deg. C. In some embodiments, the temperature can be below 200 deg. C, or alternatively below 150 deg. C, or alternatively below 100 deg. C, or alternatively below 75 deg. C. In some embodiments, the temperature can be between 25 deg. C and 100 deg. C. In some embodiments, the temperature is equal to or above the glass transition temperature (Tg) of a polymer of the stent body or a polymer of the stent coating (if applicable). In some embodiments, the temperature is equal to or above Tg but less than melting temperature of the melting temperature of the of a polymer of the stent body or a polymer of the coating. In some embodiments, a cooled or chilled fluid or gas can be used to inflate the balloon. Cooled can mean below 25 deg. C. Chilled can mean below 0 deg. C.

In some embodiments, the crimped inflation state can include hyper-inflation of the balloon. Over or hyper-inflation is defined as any diameter or size above the intended expanded configuration but less than a diameter or size which the balloon will be damaged or no longer suitable or its intended use. Balloon diameter tolerances depend on the type of balloon and the material from which the balloon is made, among other factors. The manufacturer of the balloon can provide such information to a user, for example.

Figure 2C:
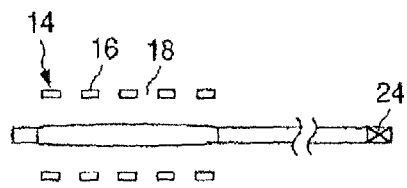
Figure 2C:
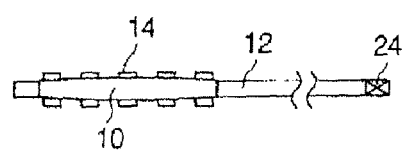
Figure 2C:
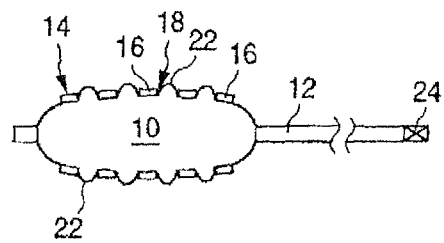

As illustrated in FIG. 2C, when the balloon 10 is inflated, it is preferred for the balloon wall or membrane to protrude out, as shown by reference number 22, from the gaps 18 between the stent struts 16. In one embodiment, the protrusion 22 should not extend beyond the outer surface of the struts 16. Alternatively, the protrusion 22 can extend beyond the outer surface of the struts 16. This ensures that the balloon wall or membrane becomes adequately wedged, lodged, squeezed, or pinched between the struts 16 when the crimping process is completed.

Figure 2D:
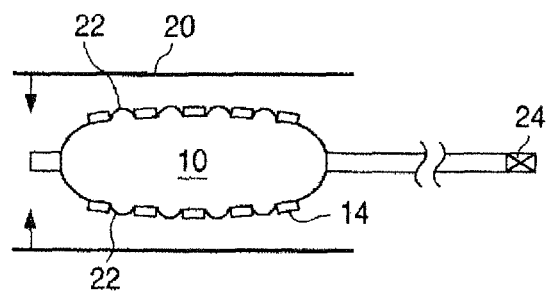

Next, as illustrated in FIG. 2D, the balloon 10 and the stent 14 are placed in the crimping device 20. Again, the balloon 10 can be inflated after being placed in the crimping device. The stent 14 can be positioned in the device 20 and held in place by application of pressure from the crimping device 20. The balloon 10 is then inserted within the stent 14. The balloon 10 is then inflated. The balloon 10 can be inflated to the inner diameter of the stent 14 or the diameter of the crimping device 20. In some embodiments, the balloon 10 can radially expand the stent 14 to a certain degree. The crimp device 20 then applies inward radial pressure to the stent 14 on the balloon 10.

Figure 2E:

The crimping device 20 can be any device used in the art. The stent 14 positioned over the balloon 10 is crimped to a reduced balloon and stent configuration (reduced crimped configuration), as illustrated in FIG. 2E. The reduced crimped configuration can be the final, desired configuration (i.e., the configuration used to introduce the device into the patient). Alternatively, reduced crimped configuration can be any configuration such that further crimping is needed. In one embodiment, the stent 14 is reduced in diameter, the balloon 10 is deflated (such as by application of a vacuum) and then re-inflated to the inner diameter of the stent 14 or diameter of the crimper. This is followed by further application of pressure by the crimping device 20. The process of application of pressure by the crimper, deflation of the balloon, re-inflation of the balloon, and application of pressure can be any number of times until the final, desired crimped state is achieved.

Crimping can be defined as the process of mounting, fastening or securing a stent on a balloon. The stent can be fixedly carried by the balloon but can be deployed by inflation and subsequent withdrawal of the balloon in order to be implanted at a target site, such as a region of stenosis. The crimp process can include selectively, radially compressing or applying pressure for positioning a stent on a balloon of a catheter assembly or an expandable delivery member of a catheter assembly. The compression or radial pressure during crimping can be segmented or uniform across the length and/or circumference of the stent. The application of pressure by the crimping device 20 can be continuous or applied in an intermittent or stepwise fashion. In an intermittent embodiment, the balloon can be deflated and re-inflated until final crimp configuration has been achieved. In some embodiments, the crimping device can hold the pressure at the reduced crimped configuration for duration of time prior to release of pressure. The process of crimping can also include, unless otherwise specifically indicated, modification made to the stent and/or balloon prior, during or subsequent to the application of crimping pressure that are directed to retention of the stent on the balloon. For example, the balloon can be coated before crimping to improve the retention of the stent on the balloon. In some embodiments, the balloon can be dipped into a fluid or solvent such as acetone before sliding the stent on the balloon in order to soften the balloon material. This makes it easy for the balloon material to squeeze into the space between the struts or structural elements. The solvents, such as acetone, may also partially dissolve the surface of the stent or coating on the stent allowing for better adhesion between the stent and the balloon. In some embodiments, a softening fluid can be used that is a non-solvent for the stent or the coating on the sent. By way of another example, a grip process can be conducted after crimping to further increase stent retention. An outer sleeve restrains the crimped stent. Simultaneously, pressure and heat are applied to the stent section. Under this action, the balloon material deforms slightly, moving in between the struts.

Reduced balloon configuration (i.e., reduced crimp configuration) is a size or diameter greater than the size or diameter of the balloon 10 in its collapsed configuration. In some embodiments, the measured reduced size or diameter can be equivalent or generally equivalent to that of the collapsed configuration. Since the balloon 10 is pressurized by a fluid or gas, a pressure release valve 24 is provided to allow release of pressure from the balloon 10 during the crimping process. During the crimping process, the pressure release valve 24 will open to release pressure when the compression pressure caused by the crimping is higher than a set value of the valve 24. The release of the pressure is controlled so as to allow the crimper 20 to apply adequate pressure on the stent 14 for fastening the stent 14 on the balloon 10. If too much pressure is released from the balloon 10 during crimping, the stent 14 may not be adequately crimped on the balloon 10. The set pressure value of the valve depends on a variety of factors including the type of crimping device, stent, and balloon used. The calculation of the amount of applied pressure and preset valve pressure intake can be readily determined by one having skilled in the art.

Figure 3:
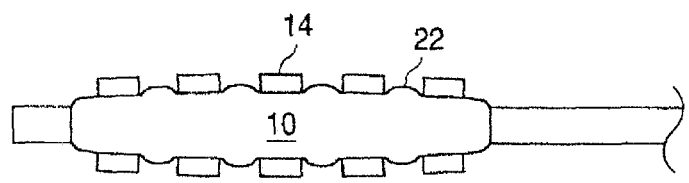
FIG. 3 illustrates an embodiment of the end result of a stent/catheter assembly produced in accordance with a method of the invention.
Figure 4A:
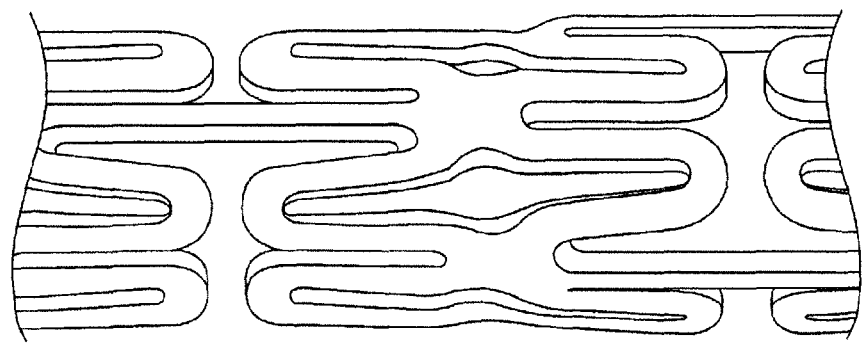
FIGS. 4A and 4B are photographs of a stent crimped on a balloon in accordance with an embodiment of the invention.
Figure 4B:
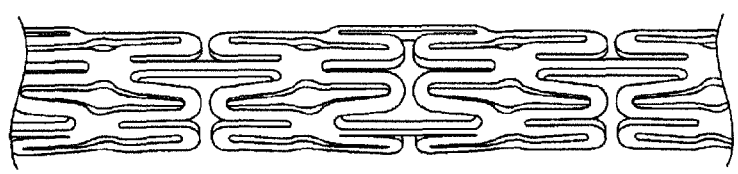

As illustrated in FIG. 3, the balloon 10, in a reduced configuration, has the stent 14 tightly crimped thereon. Balloon folds 22 have been tightly lodged, squeezed, wedged or pinched between the struts 16 of the stent 14. As the stent 14 is crimped, the struts 16 are shifted or brought closer together, causing the balloon wall or membrane 22 to be pinched between the struts 16. As for the end ring(s) of the stent 14, the balloon wall membrane 22 can be disposed between the structural elements of the stent as well. FIGS. 4A and 4B are two photographs which illustrate this crimping configuration in accordance to some embodiment of the present invention. As illustrated by the photographs, balloon wall or membrane is wedged between the structural elements of the stent In some embodiments, the stent 14 is arranged on the balloon 10 so that an outside surface of the balloon 10 and an inside surface of the stent 14 contact each other to form a combination of the balloon and stent. In some embodiments, the outer surface of the balloon or the inner surface of a stent can include a coating such as an adhesive coating, a drug delivery coating, a protective coating, a polymeric coating, a blocking agent or the like. The blocking agent is intended to reduce adhesion and/or friction between the stent 14 or a coating on the stent 14 and the balloon 10.

The stent body itself is preferably made from a polymeric material such as one or a combination of polymers. In some embodiments, such body can be made from a combination of polymeric and metallic material(s). In some embodiments, the stent is biodegradable. Both polymers and metallic materials can be biodegradable. In one preferred embodiment, the stent is completely or exclusively made from a polymeric material or combination of polymeric materials, more specifically biodegradable polymer(s). A polymeric stent can include some metallic components for allowing the stent to be viewed during the procedure; however, the amount of material is insignificant, does not impart any structural function to the stent, or for viewing means only such that the stent is in essence made from a polymeric material or combination of polymers as is understood by one having ordinary skill in the art. In some embodiments, metallic stents are completely excluded from any of the embodiments of this invention. Metallic stents have a stent body (i.e., struts or structural elements) made mostly or completely from a metallic material such as an alloy. It should be noted that biodegradable is intended to include bioabsorbable, bioerodable, etc. unless otherwise specifically indicated.

In some embodiments, the stent can include a drug coating. The coating can be a pure drug or combination of drugs. The coating can include a polymeric carrier of a single or multiple polymers. The coating can be layered as is understood by one of ordinary skilled in the art.

The stent or the coating can be made from a material including, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Another type of polymer based on poly(lactic acid) that can be used includes graft copolymers, and block copolymers, such as AB block-copolymers ("diblock-copolymers") or ABA block-copolymers ("triblock-copolymers"), or mixtures thereof.

Additional representative examples of polymers that may be especially well suited for use in fabricating or coating the stent include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known KYNAR, available from ATOFFNA Chemicals, Philadelphia, Pa.), ethylene-vinyl acetate copolymers, and polyethylene glycol.

EXAMPLE 1

A first polymer stent was crimped by in-house process. A second polymer stent was placed on a balloon and then inserted into the crimper. The crimper head was reduced to the stent's outer diameter. Then the balloon was inflated to stent's outer diameter or the crimper's inner diameter at the pressure of 30 psi. The stent was crimped down further under pressure or release pressure at a slow rate and then held at target crimping diameter for certain time without balloon pressure present.

Figure 5:
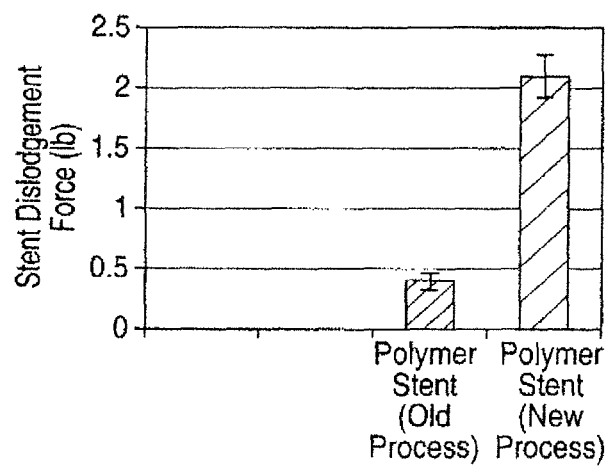
FIG. 5 is a graph illustrating the result of the Example.

Both groups were measured by Instron Tester. Bottom grip on the Instron held the balloons below the stent and the upper grip held a stent section on the balloons. The device was used to pull the stents away from the balloons by moving the upper grip in an upwards direction. The force was measured when the stents moved at least of 1 mm from the original location. FIG. 5 illustrates the result.

EXAMPLE 2

A stent can be mounted on a balloon, followed by inflating the balloon to an inner diameter of the stent. Crimp to intermediate diameter, between original diameter of the stent and final, desired diameter of the stent. The balloon can then be deflated by pulling vacuum on balloon, for example. Next, the balloon can be inflated to an intermediate diameter (diameter is controlled by position of crimping head). Crimp to final, desired diameter. This method can provide support to the stent during the initial crimping process and reduces crimping defects during the manufacturing process.

While particular embodiments of the present invention have been described, it will be obvious to those skilled in the art that changes and modifications can be made without departing from the spirit and scope of the teachings and embodiments of this invention. Therefore, the appended claims are to encompass within their scope all such changes and modifications as fall within the true spirit of this invention.

What is claimed is:

1. A method of crimping a stent onto a balloon of a catheter assembly, comprising:
    positioning a stent over a balloon of a catheter assembly, the balloon having a rated burst pressure;
    placing the stent and the balloon of the catheter assembly in a crimping device;
    inflating the balloon with an inflation fluid to a selected pressure greater than the rated burst pressure;
    crimping the stent to the balloon while the balloon is inflated to the selected pressure; and
    releasing at least a portion of the inflation fluid from the balloon.

2. The method of claim 1, wherein the wall or membrane of the balloon is pinched between stent struts across the length of the stent upon crimping of the stent to the balloon.

3. The method of claim 1, wherein the wall or membrane of the balloon is pinched between stent struts in a segmented manner across an entire length of the stent upon crimping of the stent to the balloon.

4. The method of claim 1, wherein crimping the stent comprises applying a radially compressive Force to the stent in an intermittent fashion.

5. The method of claim 1, wherein crimping the stent comprises crimping the stent to a first reduced diameter.

6. The method of claim 5, further comprising crimping the stent from the first reduced diameter to a second reduced diameter.

7. The method of claim 5, further comprising:
    deflating and re-inflating the balloon after crimping the stent to the first reduced diameter; and crimping the stent to a second reduced diameter after deflating and re-inflating the balloon.

8. The method of claim 1, wherein inflating the balloon to the selected pressure is performed before placing the stent and the balloon of the catheter assembly in the crimping device.

9. The method of claim 1, wherein inflating the balloon to the selected pressure is performed after placing the stent and the balloon of the catheter assembly in the crimping device.

10. The method of claim 1, wherein inflating the balloon to the selected pressure is performed before crimping the stent to the balloon.

11. The method of claim 1, wherein the inflation fluid is released from the balloon while crimping the stent to the balloon.

12. The method of claim 11, wherein the inflation fluid is released from the balloon controllably by a valve.

13. The method of claim 1, wherein a wall or membrane of the balloon protrudes between stent struts upon inflating the balloon to the selected pressure.

14. The method of claim 1, wherein crimping the stent to the balloon comprises applying a radially compressive force to the stent.

15. The method of claim 1, further comprising, after crimping the stent to the balloon, simultaneously applying pressure and heat to the stent and balloon.

16. The method of claim 15, wherein an outer sleeve restrains the crimped stent while simultaneously applying pressure and heat to an exterior of the stent and balloon.

17. The method of claim 1, wherein the stent is a polymeric stent.

18. The method of claim 1, wherein the stent is a biodegradable polymeric stent.

19. The method of claim 1, wherein the stent is a biodegradable polymeric stent with a biodegradable metallic component.

20. The method of claim 1, wherein the stent includes a drug coating.

21. The method of claim 1, further comprising applying a solvent to the balloon.

22. The method of claim 21, wherein the solvent is acetone.

23. The method of claim 1, further comprising applying a balloon softening fluid to the balloon.

24. The method of claim 1, wherein the balloon is inflated by a heated fluid.

25. The method of claim 1, wherein the balloon is inflated by a heated fluid having a temperature not greater than 200° C.

26. The method of claim 1, wherein the balloon is inflated by a heated fluid having a temperature not greater than 150° C.

27. The method of claim 19, wherein the balloon is inflated by a heated fluid having a temperature not greater than 100° C.

28. The method of claim 1, wherein the balloon is inflated by a heated fluid having a temperature not greater than 75° C.

* * * * *